(12) United States Patent
Moberg

(10) Patent No.: US 6,718,974 B1
(45) Date of Patent: Apr. 13, 2004

(54) CPAP HUMIDIFIER HAVING SLIDING ACCESS DRAWER

(75) Inventor: John R. Moberg, Elk River, MN (US)

(73) Assignee: Mallinckrodt, Inc., Hazelwood, MO (US)

( * ) Notice: Subject to any disclaimer, the term of this patent is extended or adjusted under 35 U.S.C. 154(b) by 65 days.

(21) Appl. No.: 09/680,864

(22) Filed: Oct. 6, 2000

(51) Int. Cl.$^7$ .............................................. A61M 15/00
(52) U.S. Cl. ........................... 128/204.14; 128/203.17; 128/204.18
(58) Field of Search ................. 128/200.14–200.24, 128/201.13, 203.12, 203.16, 203.7, 204.14, 204.18; 312/31; 126/113; 261/19, DIG. 65

(56) References Cited

U.S. PATENT DOCUMENTS

| | | | | |
|---|---|---|---|---|
| 4,361,523 A | * | 11/1982 | Shepherd | 261/92 |
| 4,921,642 A | * | 5/1990 | LaTorraca | 261/142 |
| 5,231,979 A | | 8/1993 | Rose et al. | |
| 5,343,551 A | * | 8/1994 | Glucksman | 392/405 |
| 5,564,415 A | * | 10/1996 | Dobson et al. | 128/204.14 |
| 6,189,870 B1 | * | 2/2001 | Withall | 261/62 |

* cited by examiner

Primary Examiner—Glenn K. Dawson
(74) Attorney, Agent, or Firm—Hovey Williams LLP

(57) ABSTRACT

A humidification device (10) for use with a CPAP unit (18) or similar breathing device is provided which includes a stationary cabinet (12) with a slide-type drawer member (14) adapted to hold a supply of humidifying water. The cabinet (12) includes an input (28) and an output (30) allowing connection of CPAP device conduits (100, 102) respectively for delivering air to the humidifying device (10), and for delivering humidified output air to a patient. Use of the sliding drawer member (14) facilitates filling of the device (10) with water and periodic cleanup thereof. In alternate embodiments, electrical resistance heaters (84, 86) are secured to the drawer member (14). Mating electrical connectors (42, 94) respectively mounted on the cabinet (12) and drawer member (14) provide electrical power to the heaters for water heating purposes.

16 Claims, 4 Drawing Sheets

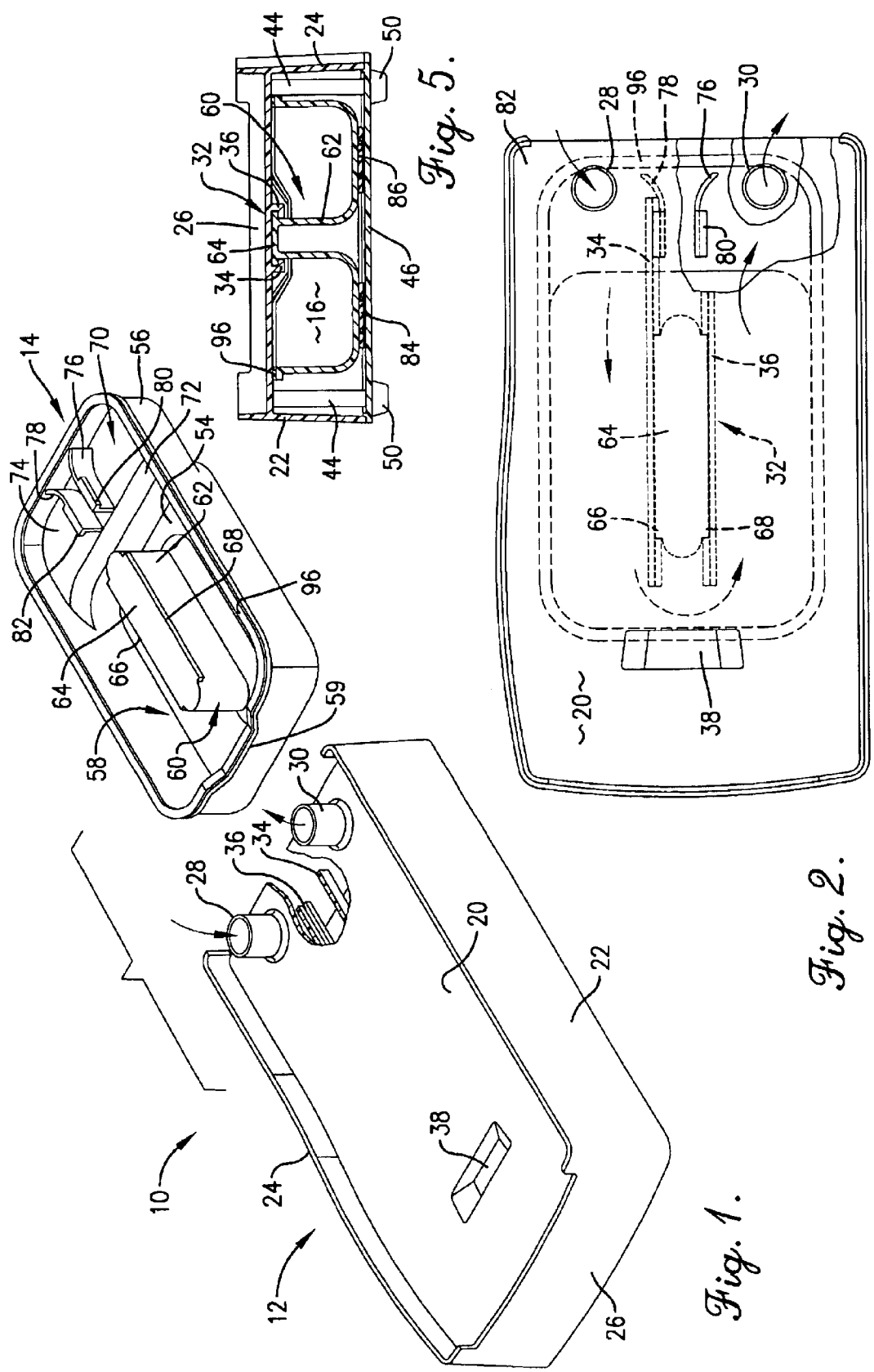

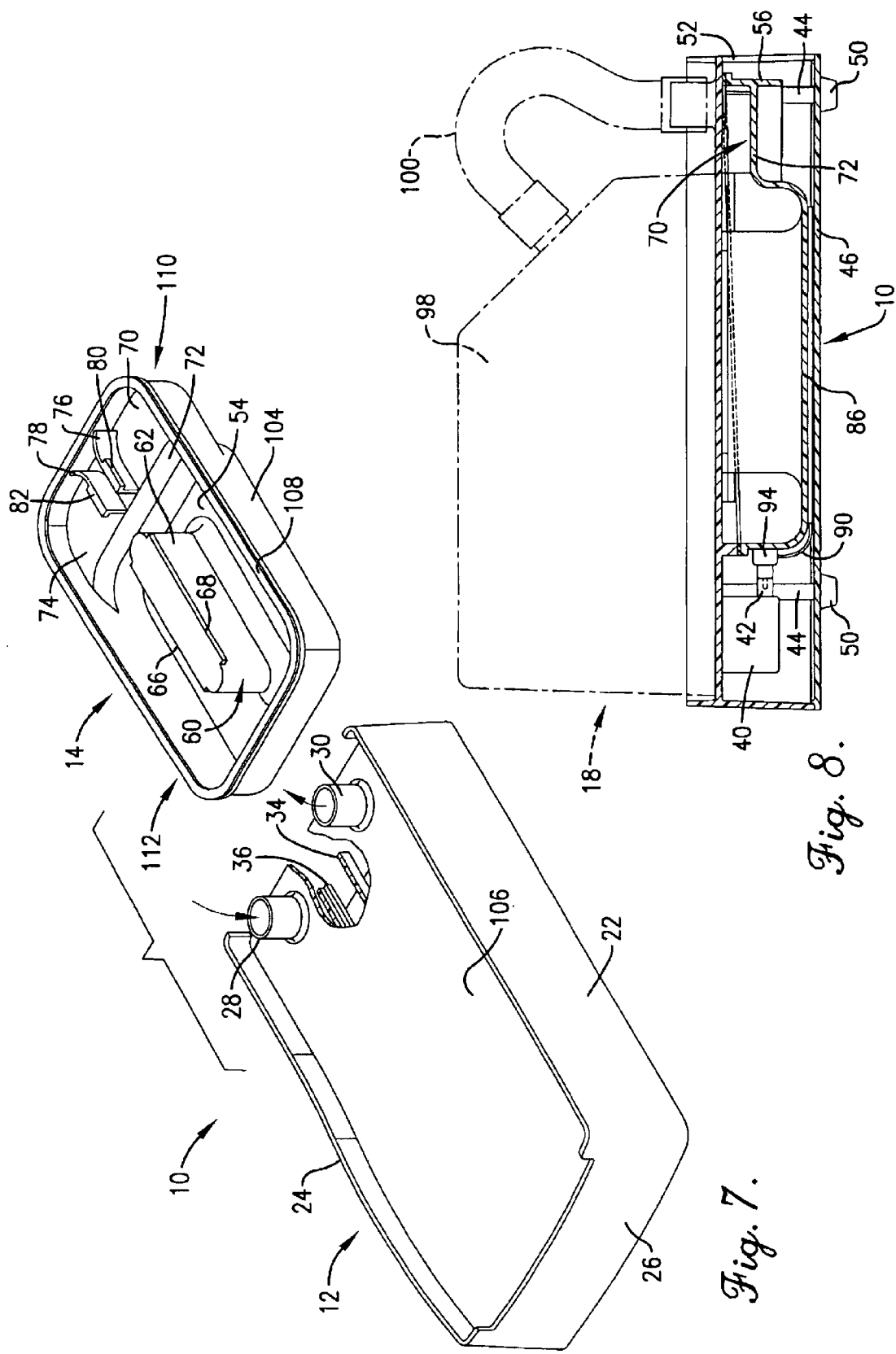

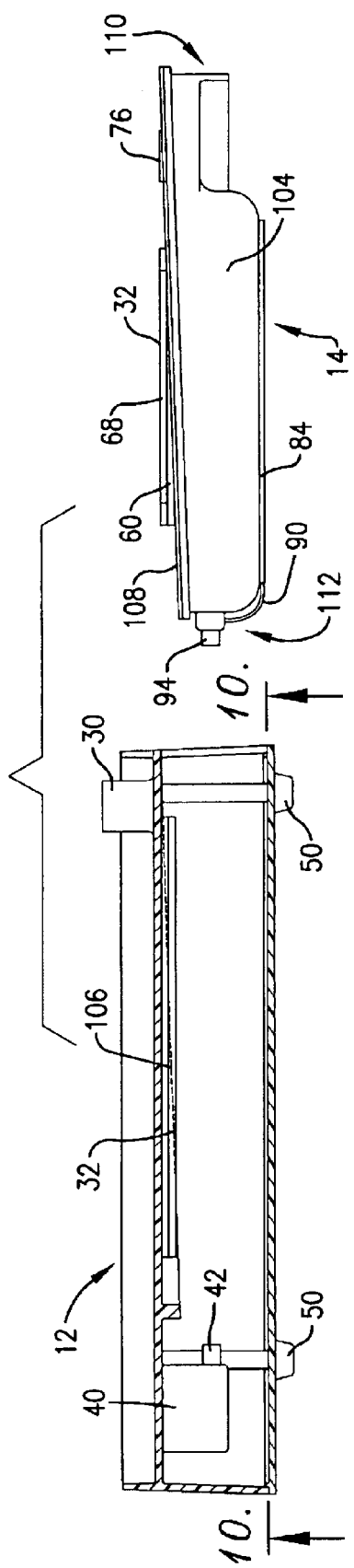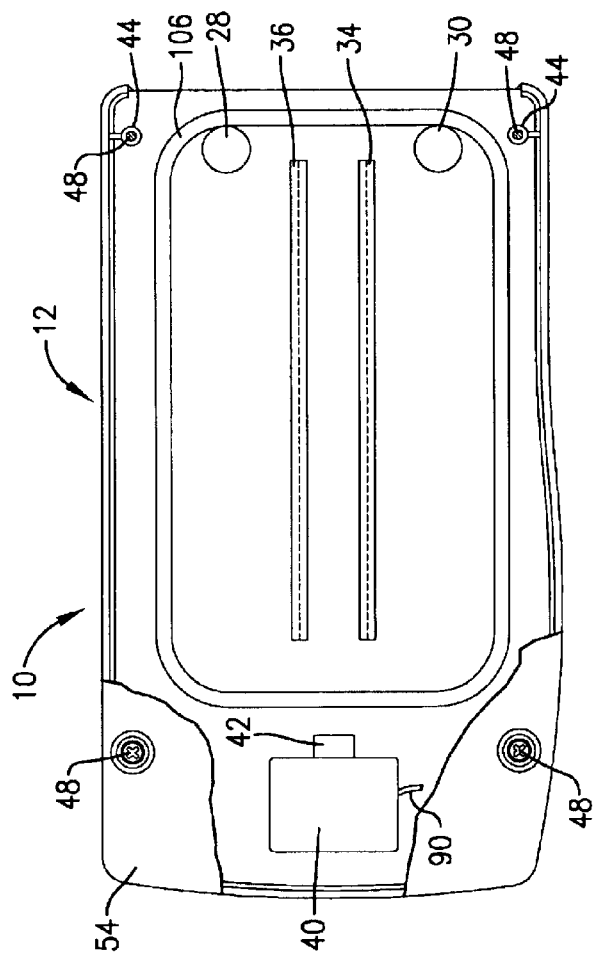

CPAP HUMIDIFIER HAVING SLIDING ACCESS DRAWER

BACKGROUND OF THE INVENTION

1. Field of the Invention

The present invention is broadly concerned with humidification devices for creating contact between an incoming gas stream and a supply of water to produce a humidified gas output. More particularly, the invention pertains to such humidification devices, especially in combination with an overall gas delivery assembly such as a CPAP (continuous positive airway pressure) unit, wherein the humidifier includes a slidable drawer member allowing easy access for filling and cleanup of the humidifier.

2. Description of the Prior Art

Sleep Apnea Syndrome is a disorder characterized by cessation of breathing and frequent awakenings during sleep. One class of sleep apnea is obstructive sleep apnea, which is characterized by the obstruction of the person's upper airway resulting in interference with breathing during sleep. In order to treat obstructive sleep apnea, CPAP devices have been developed to deliver air under constant positive pressure to the nasal passages during sleep. These devices are frequently successful in treating sleep deprivation due to obstructive sleep apnea.

In order to prevent drying of the breathing passages during the administration of CPAP, it is desirable to humidify the air supplied to the person using such devices. This may be accomplished by providing a humidifier which is essentially a bottle containing a quantity of water over which the air under pressure passes before being delivered to the user. The user partially fills the bottle with water, and the air is circulated within the bottle to pass over the surface of the water and absorb moisture therefrom.

U.S. Pat. No. 5,231,979 describes a CPAP humidifier in the form of an essentially completely enclosed body having tubular air input and output elements adjacent the forward end of the body. In order to fill the humidifier body, it is necessary to carefully pour water through one of the tubular ports until the water reaches a predetermined level. This can be troublesome and lead to water spillage. In addition, it can be difficult to clean such an enclosed humidifier body, particularly after a period of heavy use.

SUMMARY OF THE INVENTION

The present invention overcomes the problems outlined above and provides an improved humidifier for creating contact between an incoming gas stream and a supply of water so as to yield a humidified gas output stream. The humidifier is especially designed for use in conjunction with CPAP units, but may also be used with virtually any type of breathing device where humidification is desirable, e.g., ventilators.

Broadly speaking, the humidifier of the invention includes first and second slidingly interfitted members, with the second member preferably being somewhat drawer-like and adapted to hold a supply of water. The members are relatively shiftable between an open position permitting filling of the second member with water and a closed, humidifying position wherein the members cooperatively define a air-water plenum chamber. A gas input and a gas output are in communication with the plenum chamber so as to direct gas into, through and out of the plenum chamber for humidification thereof.

In preferred forms, the first member is in the form of a stationary cabinet whereas the second member comprises an open-top, water-holding drawer member. A connection assembly including mating components on the cabinet and drawer member respectively is provided for slidingly supporting the drawer member within the cabinet and permits sliding movement of the drawer member between its open and closed positions. Advantageously, the connection assembly includes a slide track supported on the cabinet whereas the drawer member has a slider which is received within the cabinet slide track. Certain embodiments of the present invention include a projection in the cabinet located at the end of the slide track. This projection mates with a recessed region of the drawer member and operates as an abutment against which the drawer contacts when inserted into the cabinet, thereby limiting further insertion of the drawer once the drawer is properly inserted into the cabinet. Other embodiments utilize a beveled drawer which is slidingly received by a cooperatively beveled cabinet. In this embodiment, the beveled drawer permits drawer insertion into the cabinet without interference from the sliding track. When the drawer is fully inserted into the cabinet, the beveled portions of the drawer engage the cooperatively beveled portions of the cabinet, thereby limiting further insertion of the drawer.

In alternate embodiments, the drawer member includes one or more resistance heaters for heating water contained therein. In this embodiment, mating electrical connectors are located on the cabinet and drawer so that, when the drawer is fully inserted within the cabinet, the connectors mate to complete a heating circuit.

The gas delivery devices (e.g., CPAP units) of the invention are designed to generate and receive patient gas and to convey such gas along a path of travel for ultimate delivery to the patient. The humidifier of the invention is designed with its gas input and output for coupling into the path of travel of gas.

BRIEF DESCRIPTION OF THE DRAWINGS

FIG. 1 is an exploded perspective view with parts broken away illustrating the components of the preferred humidifier device of the invention;

FIG. 2 is a top view of the humidifier device in its closed position with parts broken away to reveal internal construction details;

FIG. 5 is a vertical sectional view taken along line 5—5 of FIG. 3 and depicting the internal construction of the humidifier device;

FIG. 7 is an exploded perspective view with parts broken away illustrating the components of another preferred embodiment of the humidifier device of the invention;

FIG. 8 is a vertical sectional view of the embodiment of FIG. 7, illustrating a CPAP unit positioned atop the humidifier and operably coupled thereto, where the humidifier device includes water heating elements;

FIG. 9 is a sectional view of the cabinet illustrating the tapered top wall and a plan view of the drawer separated from the cabinet; and FIG. 10 is a bottom view with parts broken away of the FIG. 9 humidifier device.

DETAILED DESCRIPTION OF THE PREFERRED EMBODIMENT

Figure 3:
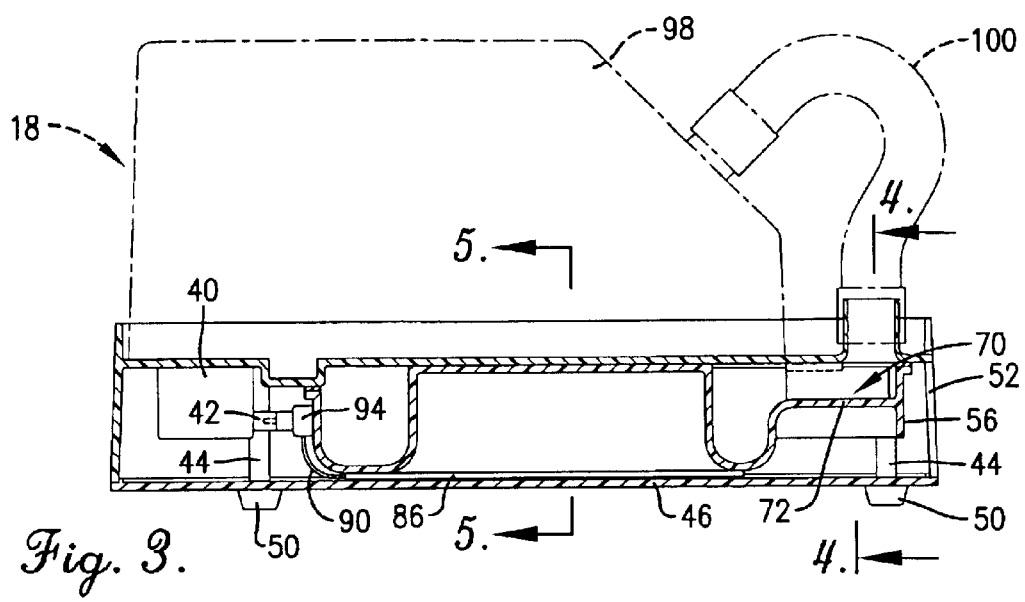
FIG. 3 is a vertical sectional view of a humidifier device similar to that depicted in FIG. 2 and illustrating a CPAP unit positioned atop the humidifier and operably coupled thereto, where the humidifier device includes water heating elements.

Turning now to the drawings, and humidifier device 10 in accordance with the invention broadly includes two slidingly interfitted members, namely a cabinet 12 and an open-top drawer member 14. The member 14 is designed to be received within cabinet 12 and is relatively shiftable between an open position permitting filling of the member 14 with water and a closed, humidifying position wherein the cabinet and drawer member cooperatively define an internal, enclosed air-water plenum chamber 16. The device 10 may be used in a variety of contexts, but is especially adapted for use with an otherwise conventional CPAP unit 18, so that pressurized air from the unit 18 is directed into and through the humidifier device 10 before delivery to a patient.

In more detail, the cabinet 12 is preferably an integral body formed of an appropriate synthetic resin material, having a top wall 20 as well as a depending sidewalls 22, 24 and end wall 26. As best seen in FIG. 1, the walls 22–26 project above the upper surface of top wall 20. The top wall is configured with a tubular air inlet 28 and a spaced, tubular air outlet 30 adjacent the front open end of the cabinet and which communicate with the interior thereof. The inner or lower face of top wall 20 has an elongated, centrally located sliding track 32 formed of a pair of elongated, somewhat L-shaped projections 34, 36. In some embodiments, top wall 20 includes an inwardly extending, somewhat trapezoidally shaped projection 38 disposed rearwardly of the inner end of track 32. This projection provides an abutment which limits insertion of member 14.

In the embodiment of FIGS. 3–6, a circuit box 40 including an electrical connector 42 is secured to the inner face of top wall 20 rearward of projection 38. The box 40 is adapted to be coupled with a conventional power source and is designed to control the operation of the drawer member heaters later to be described.

The cabinet 12 has four tubular, internally threaded connectors 44 at approximately the corners thereof. A base plate 46 is secured to the connectors 44 by means of screws 48, to complete the cabinet 12. The lower face of base plate 46 is equipped with corner-mounted support feet 50 as shown. As best seen in FIG. 3, the cabinet 12 is thus a substantially enclosed body, except for a generally rectangular drawer member entrance opening 52 at the forward end thereof.

Figure 4:
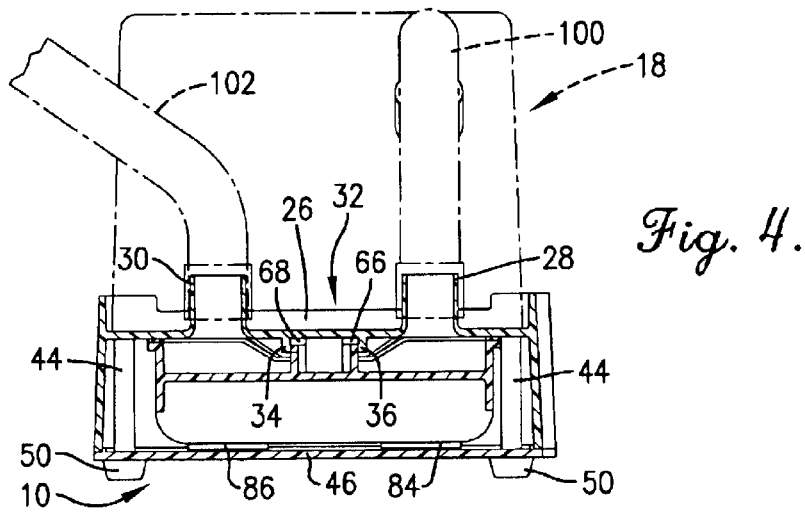
FIG. 4 is a vertical sectional view taken along line 4—4 of FIG. 3 and further illustrating details of the humidifier and associated CPAP device.
Figure 6:
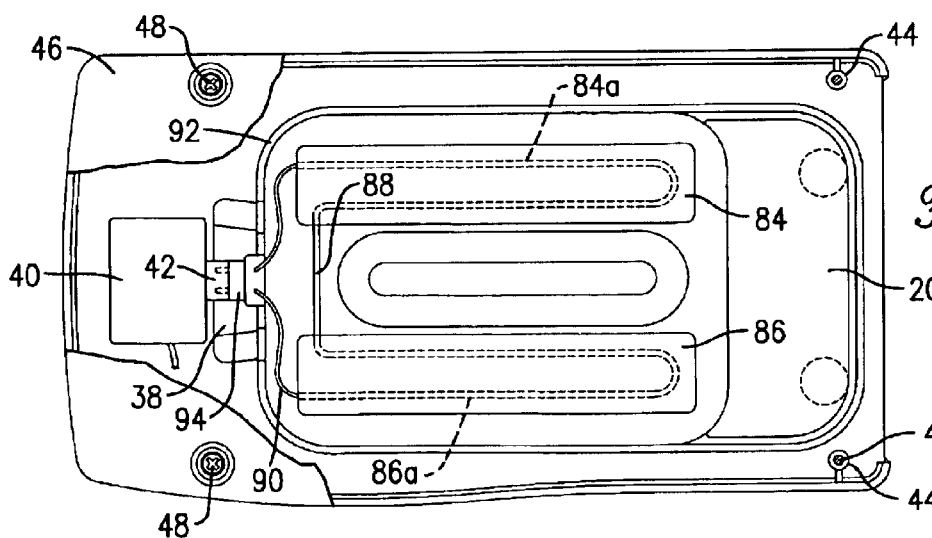
FIG. 6 is a bottom view with parts broken away of the FIG. 3 humidifier device, illustrating the electrical circuitry associated with the humidifier heater.

The drawer member 14 as indicated is adapted to be slidingly received within cabinet 12. The drawer member is in the form of a molded synthetic resin body presenting a bottom wall 54 and an upstanding, circumscribing sidewall 56 to thereby define a water holding area 58; the rear segment of sidewall 56 includes a recessed region 59 adapted to mate with cabinet projection 38 and permit insertion of drawer 14 past sliding track 32 without obstruction between sidewall 56 and track 32. Additionally, mating of recessed region 59 and cabinet projection 38 provides a seal between cabinet 12 and drawer 14. It will be observed that the bottom wall 54 includes an elongated, upstanding hollow slider 60 having a continuous sidewall 62 and top wall 64. The side margins of top wall 64 extend beyond the sidewall 62 a short distance to define laterally projecting flanges 66, 68. As best seen in FIG. 4, the flanges 66, 68 are adapted for sliding reception within the projections 34, 36 making up slide track 32.

The drawer member 14 also includes a forward ledge segment 70 defined by an upstanding wall portion 72 and horizontally extending shelf wall 74 leading to and merging with the sidewall 56. The ledge segment 70 supports a pair of opposed, upwardly extending engagement walls 76, 78. As illustrated, the rearward axially extending ends of the walls 76, 78 include respective flange projections 80, 82 which are oriented to fit within the forward ends of the cabinet projections 34, 36.

The drawer member 14 of the FIGS. 3–6 embodiment is equipped with a pair of elongated, plate-like heaters 84, 86 which are respectively adhered to the underside of bottom wall 54 astride the hollow opening defined by upstanding projection 60 (see FIG. 5). The heaters 84, 86 include an internal resistance heating element 84a, 86a which are interconnected by lead 88. Additionally, leads 90, 92 extend from the heating elements 84a, 86a to a rigidly mounted electrical connector 94 mounted on the rear segment of sidewall 56. The connector 94 is designed to mate with connector 42 when drawer member 14 is slid into cabinet 12.

The upper margin of drawer member sidewall 56 includes a continuous rubber-like resilient seal 96 which extends about the entire periphery of the drawer member. The seal 96 is adapted to engage the underside of cabinet top wall 20 when the drawer member is operatively inserted into the cabinet 12.

The CPAP device 18 is of conventional design and is adapted to sit atop the humidification device 10 on cabinet top wall 20. The CPAP device 18 is designed to deliver positive pressure air from a main housing 98 to inlet 28 via conduit 100. As shown, the conduit 100 is coupled with humidifier inlet 28. Another conduit 102 is coupled with humidifier outlet 30 and leads to a patient. A variety of different CPAP devices have been developed in the past and are well known to those skilled in the art.

Another embodiment of the CPAP device 18 of the present invention is illustrated in FIGS. 7–10. In this embodiment, cabinet 12 is formed without projection 38 and drawer 14 is formed without recessed region 59. Therefore, in order to limit insertion of drawer 14, drawer 14 is provided with a beveled or tapered sidewall 104, best seen in FIG. 9, which engages the cooperatively beveled or tapered underside of cabinet top wall 106 when drawer 14 is properly inserted into cabinet 12. A continuous rubber-like resilient seal 108 is included atop sidewall 104. Advantageously, circumscribing beveled sidewall 104 permits insertion of drawer 14 into cabinet 12 without interference from slide track 32. The cooperatively tapered sidewall 104 and top wall 106 also permit drawer 14 to be inserted into cabinet 12 without obstruction between sidewall 104 and track 32. Accordingly, sidewall 104 is angled slightly downward from front sidewall portion 110 to rear sidewall portion 112. Alternatively, seal 108 may be slightly thicker near portion 112 in order to account for the downward slope of sidewall 104 and engage top wall 106, thereby preventing passage of water from drawer member 14.

In the use of humidifying device 10, it will be assumed that the CPAP device 18 is sitting atop cabinet 12 as shown in FIGS. 3–4, with the conduits 100, 102 connected as shown. The user first grasps drawer member 14, typically by placing the fingers beneath ledge segment 70 and behind the forward portion of drawer sidewall 56. The drawer member 14 is then pulled outwardly until the water holding area 58 becomes accessible. This area is filled with water up to approximately the level of ledge segment 70 whereupon the user pushes the drawer member back into its recessed position within cabinet 12. As this occurs, the seal 96, 108 prevents passage of water from the drawer member 14. As the drawer member assumes its operative position depicted in FIGS. 3 and 8, the connector 94 mates with connector 42, thus establishing an electrical connection between circuitry 40 and the heaters 84, 86. These heaters can then be actuated, typically through a conventional on-off switch (not shown). The heaters 84, 86 warm the water within area 58.

The user then dons a CPAP nose mask or other similar device, which is coupled to the remote end of conduit 102. As pressurized air from the CPAP device 18 is generated, it is passed through conduit 100 and inlet 28 into plenum chamber 16 where it is humidified in the presence of the water therein. Humidified air exits from outlet 30 and is conveyed to the patient via conduit 102.

In the embodiment of FIGS. 1–2 which does not include the heaters and its associated hardware and circuitry, the use is similar, except that when the drawer member 14 is slid into cabinet 12, there is no electrical component interconnection and thus no heating of the water within the drawer member.

I claim:

1. A gas delivery device adapted to be coupled with a patient for delivery of gas to the patient, said device comprising:

a gas delivery assembly adapted to receive patient gas and to convey the gas along a path of travel to said patient; and a humidifier for creating contact between said patient gas and a supply of water in order to produce a humidified gas output stream, said humidifier including first and second slidingly interfitted members, each of said members having a length and a height, said second member being adapted to hold a supply of water, said members being relatively shiftable along an axis that is substantially parallel to the axis along the length of said second member between an open position permitting filling of said second member with water and a closed, humidifying position wherein the members cooperatively define an air-water plenum chamber, there being a gas input and a gas output in communication with said plenum chamber for coupling the humidifier into said path of travel, wherein said first member comprises a cabinet, said second member comprises an open top drawer member adapted to hold a supply of water, there being a connection assembly including components on said cabinet and drawer member respectively and operable for slidingly supporting said drawer member within said cabinet and permitting selective sliding movement of the drawer member between said open position and said closed position, said drawer member having a bottom wall, an upstanding sidewall presenting an upper margin, and a resilient seal adjacent said upper margin for sealingly engaging said cabinet when said drawer member is in said closed position.

2. A gas delivery device adapted to be coupled with a patient for delivery of gas to the patient, said device comprising:

a gas delivery assembly adapted to receive patient gas and to convey the gas along a path of travel to said patient; and a humidifier for creating contact between said patient gas and a supply of water in order to produce a humidified gas output stream, said humidifier including first and second slidingly interfitted members, each of said members having a length and a height, said second member being adapted to hold a supply of water, said members being relatively shiftable along an axis that is substantially parallel to the axis along the length of said second member between an open position permitting filling of said second member with water and a closed, humidifying position wherein the members cooperatively define an air-water plenum chamber, there being a gas input and a gas output in communication with said plenum chamber for coupling the humidifier into said path of travel, wherein said first member comprises a cabinet, said second member comprises an open top drawer member adapted to hold a supply of water, there being a connection assembly including components on said cabinet and drawer member respectively and operable for slidingly supporting said drawer member within said cabinet and permitting selective sliding movement of the drawer member between said open position and said closed position, said cabinet having an upper, generally horizontal wall, depending sidewalls and a depending end wall, said upper wall and sidewalls cooperatively defining an entrance opening, said upper wall including a slide track, said drawer member including a bottom wall and an upstanding sidewall presenting an upper margin with a proximal resilient seal, there being an upright slider supported by said drawer member bottom wall, said slider interfitting with said slide track and with said seal engaging said cabinet upper wall.

3. The device of claim 2, said gas input and said gas output comprising respective tubular extensions on said cabinet upper wall and communicating with the interior of the cabinet.

4. A gas delivery device adapted to be coupled with a patient for delivery of gas to the patient, said device comprising:

a gas delivery assembly adapted to receive patient gas and to convey the gas along a path of travel to said patient; and a humidifier for creating contact between said patient gas and a supply of water in order to produce a humidified gas output stream, said humidifier including first and second slidingly interfitted members, each of said members having a length and a height, said second member being adapted to hold a supply of water, said members being relatively shiftable along an axis that is substantially parallel to the axis along the length of said second member between an open position permitting filling of said second member with water and a closed, humidifying position wherein the members cooperatively define an air-water plenum chamber, there being a gas input and a gas output in communication with said plenum chamber for coupling the humidifier into said path of travel, said humidifier further including a heater operatively disposed to heat said water within said plenum chamber.

5. The device of claim 4, said heater mounted on said second member.

6. The device of claim 4, including control circuitry coupled with said heater for initiating the operation of the heater when said members are in said closed, humidifying position.

7. A humidifier for creating contact between an incoming gas stream and a supply of water in order to produce a humidified gas output stream, said humidifier including first and second slidingly interfitted members, said second slidingly interfitted member permitting sliding along an axis which is substantially parallel to the axis of the length thereof, said second member being adapted to hold a supply of water, said members being relatively shiftable between an open position permitting filling of said second member with water and a closed, humidifying position wherein the members cooperatively define an air-water plenum chamber, there being a gas input and a gas output in communication with said plenum chamber for conveying said gas into and through said plenum chamber for humidification thereof, said first member comprising a cabinet, said second member comprising an open top drawer member adapted to hold a supply of water, there being a connection assembly including components on said cabinet and drawer member respectively and operable for slidingly supporting said drawer member within said cabinet and permitting selective sliding movement of the drawer member between said open position and said closed position, said drawer member having a bottom wall, an upstanding sidewall presenting an upper margin, and a resilient seal adjacent said upper margin for sealingly engaging said cabinet when said drawer member is in said closed position.

8. A humidifier for creating contact between an incoming gas stream and a supply of water in order to produce a humidified gas output stream, said humidifier including first and second slidingly interfitted members, said second slidingly interfitted member permitting sliding along an axis which is substantially parallel to the axis of the length thereof, said second member being adapted to hold a supply of water, said members being relatively shiftable between an open position permitting filling of said second member with water and a closed, humidifying position wherein the members cooperatively define an air-water plenum chamber, there being a gas input and a gas output in communication with said plenum chamber for conveying said gas into and through said plenum chamber for humidification thereof said first member comprising a cabinet, said second member comprising an open top drawer member adapted to hold a supply of water, there being a connection assembly including components on said cabinet and drawer member respectively and operable for slidingly supporting said drawer member within said cabinet and permitting selective sliding movement of the drawer member between said open position and said closed position, said cabinet having an upper, generally horizontal wall, depending sidewalls and a depending end wall, said upper wall and sidewalls cooperatively defining an entrance opening, said upper wall including a slide track, said drawer member including a bottom wall and an upstanding sidewall presenting an upper margin with a proximal resilient seal, there being an upright slider supported by said drawer member bottom wall, said slider interfitting with said slide track and with said seal engaging said cabinet upper wall.

9. The humidifier of claim 8, said gas input and said gas output comprising respective tubular extensions on said cabinet upper wall and communicating with the interior of the cabinet.

10. A humidifier for creating contact between an incoming gas stream and a supply of water in order to produce a humidified gas output stream, said humidifier including first and second slidingly interfitted members, said second slidingly interfitted member permitting sliding along an axis which is substantially parallel to the axis of the length thereof, said second member being adapted to hold a supply of water, said members being relatively shiftable between an open position permitting filling of said second member with water and a closed, humidifying position wherein the members cooperatively define an air-water plenum chamber, there being a gas input and a gas output in communication with said plenum chamber for conveying said gas into and through said plenum chamber for humidification thereof, the humidifier further including a heater operatively disposed to heat said water within said plenum chamber.

11. The humidifier of claim 10, said heater mounted on said second member.

12. The humidifier of claim 10, including control circuitry coupled with said heater for initiating the operation of the heater when said members are in said closed, humidifying position.

13. A gas delivery device adapted to be coupled with a patient for delivery of gas to the patient, said device comprising:

a gas delivery assembly adapted to receive patient gas and to convey the gas along a path of travel to said patient; and a humidifier for creating contact between said patient gas and a supply of water in order to produce a humidified gas output stream, said humidifier including first and second slidingly interfitted members, said first member comprising a cabinet, said second member comprising an open top drawer member adapted to hold a supply of water, said members being relatively shiftable between an open position permitting filling of said second member with water and a closed, humidifying position wherein the members cooperatively define an air-water plenum chamber, said cabinet having an upper, generally horizontal wall, depending sidewalls and a depending end wall, said upper wall and sidewalls cooperatively defining an entrance opening, said upper wall including a slide track, said drawer member including a bottom wall and an upstanding sidewall presenting an upper margin with a proximal resilient seal, there being an upright slider supported by said drawer member bottom wall, said slider interfitting with said slide track and with said seal engaging said cabinet upper wall, there being a gas input and a gas output in communication with said plenum chamber for coupling the humidifier into said path of travel and there being a connection assembly including components on said cabinet and said drawer member respectively and operable for slidingly supporting said drawer member within said cabinet and permitting selective sliding movement of the drawer member between said open position and said closed position.

14. The device of claim 13, said gas input and said gas output comprising respective tubular extensions on said cabinet upper wall and communicating with the interior of the cabinet.

15. A humidifier for creating contact between an incoming gas stream and a supply of water in order to produce a humidified gas output stream, said humidifier including first and second slidingly interfitted members, said second member being adapted to hold a supply of water, said members being relatively shiftable between an open position permitting filling of said second member with water and a closed, humidifying position wherein the members cooperatively define an air-water plenum chamber, said first member comprising a cabinet, said cabinet having an upper, generally horizontal wall, depending sidewalls and a depending end wall, and upper wall and sidewalls cooperatively defining an entrance opening, said upper wall including a slide track, said drawer member including a bottom wall and upstanding sidewall presenting an upper margin with a proximal resilient seal, there being an upright slider supported by said drawer member bottom wall, said slider interfitting with said slide track and with said seal engaging said cabinet upper wall, said second member comprising an open top drawer member, there being a connection assembly including components on said cabinet and said drawer member respectively and operable for slidingly supporting said drawer member within said cabinet and permitting selective sliding movement of the drawer member between said open position and said closed position, there being a gas input and a gas output in communication with said plenum chamber for conveying said gas into and through said plenum chamber for humidification thereof.

16. The humidifier of claim 15, said gas input and said gas output comprising respective tubular extensions on said cabinet upper wall and communicating with the interior of the cabinet.

\* \* \* \* \*